(12) United States Patent
Lupton (10) Patent No.: US 10,136,914 B2
(45) Date of Patent: Nov. 27, 2018

(54) ANCHORING DEVICE FOR ANCHORING A BORING TOOL IN A LUMEN OR VESSEL

(76) Inventor: Henry William Lupton, Oranmore (IE)

( * ) Notice: Subject to any disclaimer, the term of this patent is extended or adjusted under 35 U.S.C. 154(b) by 544 days.

(21) Appl. No.: 14/004,720

(22) PCT Filed: Mar. 15, 2012

(86) PCT No.: PCT/IE2012/000012
§ 371 (c)(1),
(2), (4) Date: Oct. 28, 2013

(87) PCT Pub. No.: WO2012/123930
PCT Pub. Date: Sep. 20, 2012

(65) Prior Publication Data
US 2014/0058421 A1    Feb. 27, 2014

(30) Foreign Application Priority Data
Mar. 15, 2011  (IE) .................................. S2011/0123

(51) Int. Cl.
A61B 17/22      (2006.01)
A61B 17/3207    (2006.01)
(Continued)

(52) U.S. Cl.
CPC .. *A61B 17/320758* (2013.01); *A61B 17/3207* (2013.01); *A61M 25/04* (2013.01);
(Continued)

(58) Field of Classification Search
CPC .............. A61M 25/1006; A61M 25/04; A61M 25/0194; A61M 2025/1047;
(Continued)

(56) References Cited

U.S. PATENT DOCUMENTS 4,793,348 A * 12/1988 Palmaz ..................... A61F 2/01
606/1
2004/0254597 A1   12/2004 Schwartz et al.
(Continued)

FOREIGN PATENT DOCUMENTS

EP     0 234 951 A1   9/1987
WO    2008/070262 A2   6/2008
WO    2009/120205 A1  10/2009

OTHER PUBLICATIONS

International Search Report of PCT/IE2012/00012, dated Oct. 8, 2012.

*Primary Examiner* — Jonathan Miles
*Assistant Examiner* — Wade Miles
(74) *Attorney, Agent, or Firm* — Sughrue Mion, PLLC (57) ABSTRACT

An anchoring device (1) for anchoring a boring tool (3) in a lumen (4) for boring through an occlusion (6) in the lumen (4) comprises an expandable element (18) adapted for securing to a balloon (12) of a balloon catheter (8) adjacent a distal end (7) thereof. The expandable element (18) is expandable and contractible with the balloon (12) of the balloon catheter (8) for engaging the lumen and for anchoring the anchoring device (1) in the lumen (4). A guide element (33) extends coaxially from the expandable element (18), and a guide bore (34) extending through the guide element (33) is provided with an internal primary screw thread (35) for engaging a corresponding external screw thread (36) on the boring tool (3). A carrier wire (45) extends from the boring tool (3) through a central lumen (15) of the balloon catheter (8), so that rotation of the boring tool (3) by the guide wire (45) when the threads (35,36) are engaged results in the boring tool being urged through the occlusion (6) for forming an opening therethrough.

17 Claims, 6 Drawing Sheets

(51) Int. Cl.
*A61M 25/04* (2006.01)
*A61F 2/958* (2013.01)
*A61M 25/10* (2013.01)
*A61B 90/00* (2016.01)

(52) U.S. Cl.
CPC ............ *A61B 2017/22069* (2013.01); *A61B 2017/22094* (2013.01); *A61B 2017/22095* (2013.01); *A61B 2090/08021* (2016.02); *A61F 2/958* (2013.01); *A61M 2025/1052* (2013.01)

(58) Field of Classification Search
CPC .. A61M 2025/1054; A61M 2025/1052; A61M 2025/1084; A61M 2025/1081; A61B 17/3207; A61B 17/320758; A61B 2017/320766; A61F 2/958; A61F 2/01; A61F 2002/016; A61F 2002/011; A61F 2002/9583; A61F 2002/9586
See application file for complete search history.

(56) References Cited

U.S. PATENT DOCUMENTS

| | | |
|---|---|---|
| 2006/0293612 A1 | 12/2006 | Jenson et al. |
| 2009/0306597 A1 | 12/2009 | Lupton et al. |
| 2011/0125181 A1* | 5/2011 | Brady .............. A61B 17/22031 606/200 |

* cited by examiner

ANCHORING DEVICE FOR ANCHORING A BORING TOOL IN A LUMEN OR VESSEL

CROSS REFERENCE TO RELATED APPLICATIONS

This application is a National Stage of International Application No. PCT/IE2012/000012 filed Mar. 15, 2012, claiming priority based on Irish Patent Application No. S2011/0123, filed Mar. 15, 2011, the contents of all of which are incorporated herein by reference in their entirety.

The present invention relates to an anchoring device and a method for anchoring a boring tool in a lumen or vessel, and the invention also relates to an adapter for attaching to a balloon catheter for anchoring a boring tool in a lumen or vessel. The invention also relates to a combination of the adapter and a balloon catheter for anchoring a boring tool in a lumen or vessel, and the invention further relates to a combination of an anchoring device or an adapter and a boring tool. Further the invention relates to a combination of the anchoring device and a delivery device for delivering the anchoring device to a remote site in a lumen or vessel.

Occlusion of blood vessels results from a variety of tissue growth within the vessel. The tissue can become dense and fibrous, and its surface can calcify and harden. The most common minimally invasive treatment for unblocking such vessels is a treatment which is referred to as angioplasty. In an angioplasty treatment a balloon catheter is inserted into the arterial or venal system, typically through one of the femoral arteries or the radial arteries, and is passed through the arterial or venal system to the occluded site. The balloon catheter terminates in a leading portion which carries a balloon, and the leading portion is urged through the occlusion so that the balloon in a deflated state is positioned in the occlusion. Inflating of the balloon dilates the occluded vessel, and a stent, which typically is of tubular wire mesh construction is carried on the exterior of the balloon and is expanded by the inflating of the balloon. The expanded stent remains in place in the expanded state in the occluded region after deflation of the balloon. The stent acts as an implanted scaffold within the vessel for maintaining the occluded region of the vessel dilated.

However, in order to carry out an angioplasty treatment, the blockage must first be traversed by a wire, typically, a guide wire, which acts as a rail over which the balloon catheter is advanced to the occlusion. Failure to cross the occlusion with the guide wire or to position the balloon catheter with the balloon located within the occlusion requires reverting to traditional surgical invasive techniques in order to unblock the occlusion.

Typically, in an angioplasty treatment the guide wire which is advanced to the occluded vessel is a relatively stiff wire, and where the occlusion is relatively soft, manually urging the guide wire in its axial direction is sufficient to urge the guide wire through the occlusion. However, in cases where the occlusion becomes calcified and hardened, it is necessary to employ a laser catheter or a radio frequency guide wire in an attempt to pass through the occlusion. Such laser catheters and radio frequency guide wires require relatively expensive external power packs, and also require highly trained personnel for their operation.

Additionally, known minimally invasive systems for unblocking an occlusion must be controlled externally of the body by pushing the guide wire through a catheter, which may or may not be a balloon catheter. Thus, control of the tip of the guide wire which is being urged through the occlusion is arbitrary, and there is no guarantee that the tip of the guide wire remains in a substantially central position within the vessel as it is being advanced into engagement with the occlusion. Indeed, it is not uncommon for a guide wire as it is being advanced into engagement with an occlusion, and in particular a relatively hard occlusion, to slide to one side of the occlusion, and thus, lead to dissection of the blood vessel where the tip of the guide wire passes through the wall of the blood vessel, thus separating an inner lining of the wall of the blood vessel from the outer lining. This can create a false lumen within the wall of a blood vessel. In extreme cases the guide wire on slipping to the side of the occlusion, may extend through and exit the wall of the blood vessel, thus perforating the blood vessel, which results in internal bleeding. This problem is further compounded when the occluded vessel is within the cardiovascular system, since the heart moves as it beats, and thus, it is virtually impossible to maintain the tip of the guide wire centrally in the occluded vessel.

U.S. published Patent Application Specification No. 2009/0306597 of the present applicant and another discloses a device for unblocking an occluded lumen or vessel at a remote site having an occlusion therein. However, the device disclosed in this U.S. specification is a special purpose device, and is suitable only for this particular task, and is relatively expensive.

It would therefore be advantageous if a less expensive device were available which could be attached to other equipment which is readily available in an operating theatre for use with a boring tool for unblocking an occlusion.

The present invention is directed towards providing an anchoring device and a method for anchoring a boring tool in a lumen or vessel, and the invention is also directed towards an adapter for attaching to a balloon catheter for anchoring a boring tool in a lumen or vessel. The invention is also directed towards a combination of the adapter and a balloon catheter for anchoring a boring tool in a lumen or vessel, and the invention is further directed towards a combination of an anchoring device or an adapter and a boring tool. Further the invention is directed towards a combination of the anchoring device and a delivery device for delivering the anchoring device to a remote site in a lumen or vessel.

According to the invention there is provided an anchoring device for anchoring a boring tool at a site in a lumen or vessel, the anchoring device comprising an expandable element adapted for expanding in the lumen or vessel to anchor the anchoring device therein, the expandable element being adapted for securing to a delivery device for delivering the anchoring device to the site in the lumen or vessel, a guide element defining a guide bore extending therethrough to accommodate one of a boring tool and a carrier element of the boring tool for guiding the boring tool, and an engagement means associated with one of the guide element and the expandable element for engaging one of the boring tool and the carrier element of the boring tool so that the boring tool is urgeable outwardly of the guide element against the anchoring device.

In one aspect of the invention the expandable element defines a main central axis, and the guide bore of the guide element defines a secondary central axis.

In one embodiment of the invention the guide element is configured relative to the expandable element with the secondary central axis defined by the guide bore of the guide element extending substantially parallel to the main central axis defined by the expandable element.

In another embodiment of the invention the guide element is configured relative to the expandable element with the secondary central axis defined by the guide bore of the guide element substantially coinciding with the main central axis defined by the expandable element.

In an alternative embodiment of the invention the guide element is configured relative to the expandable element with the secondary central axis defined by the guide bore of the guide element offset from the main central axis defined by the expandable element.

In another alternative embodiment of the invention the guide element is configured relative to the expandable element with the secondary central axis defined by the guide bore of the guide element extending at an angle greater than zero to the main central axis defined by the expandable element.

Preferably, the guide element is configured relative to the expandable element with the secondary central axis defined by the guide bore of the guide element extending at an angle between 1° and 90° to the main central axis defined by the expandable element.

In one embodiment of the invention the guide element is configured relative to the expandable element with the secondary central axis defined by the guide bore of the guide element extending at an angle between 20° and 35° to the main central axis defined by the expandable element. Preferably, the guide element is configured relative to the expandable element with the secondary central axis defined by the guide bore of the guide element extending at an angle of approximately 30° to the main central axis defined by the expandable element.

In another embodiment of the invention the guide element is configured relative to the expandable element with the secondary central axis defined by the guide bore of the guide element extending at an angle between 35° and 55° to the main central axis defined by the expandable element. Preferably, the guide element is configured relative to the expandable element with the secondary central axis defined by the guide bore of the guide element extending at an angle of approximately 45° to the main central axis defined by the expandable element.

In a further embodiment of the invention the guide element is configured relative to the expandable element with the secondary central axis defined by the guide bore of the guide element extending at an angle between 55° and 70° to the main central axis defined by the expandable element. Preferably, the guide element is configured relative to the expandable element with the secondary central axis defined by the guide bore of the guide element extending at an angle of approximately 60° to the main central axis defined by the expandable element.

In a still further embodiment of the invention the guide element is configured relative to the expandable element with the secondary central axis defined by the guide bore of the guide element extending at an angle between 70° and 90° to the main central axis defined by the expandable element. Preferably, the guide element is configured relative to the expandable element with the secondary central axis defined by the guide bore of the guide element extending at an angle of approximately 90° to the main central axis defined by the expandable element.

In one aspect of the invention the guide element extends from the expandable element. In another aspect of the invention the guide element is located within the expandable element.

In one embodiment of the invention the engagement means comprises an internal primary screw thread located in one of the guide bore and the expandable element. Preferably, the primary screw thread is adapted for engaging a corresponding external screw thread on one of the boring tool and the carrier element of the boring tool.

In one embodiment of the invention the engagement means is located in the guide bore of the guide element.

Preferably, the expandable element is reversibly expandable. Advantageously, the expandable element is expandable in response to radial outward pressure acting thereon. Ideally, the expandable element is of a resilient material.

In one embodiment of the invention the expandable element is adapted for releasable securing to an expandable member of the delivery device.

Preferably, the expandable element is adapted for mounting on an expandable member of the delivery device. Advantageously, the expandable element is adapted for engaging an expandable member of the delivery device. Preferably, the expandable element is adapted for releasably engaging an expandable member of the delivery device.

In one aspect of the invention the expandable element is adapted for engaging an outer surface of an expandable member of the delivery device.

In another aspect of the invention a securing means is provided for securing the expandable element on an expandable member of the delivery device. Preferably, the securing means is adapted for releasably securing the expandable element on the expandable member of the delivery device. Advantageously, the securing means comprises a friction surface formed internally in the expandable element. Ideally, the securing means comprises at least one circumferentially extending ridge extending inwardly from the internal surface of the expandable element.

Alternatively, the securing means comprises a secondary screw thread. Preferably, the secondary screw thread is of an opposite hand to the primary screw thread.

In another aspect of the invention a stop means is provided for preventing relative rotation between the expandable element and the delivery device. Preferably, the stop means comprises at least one longitudinally extending ridge extending inwardly from the internal surface of the expandable element.

Advantageously, the expandable element is expandable with an expandable member of the delivery device.

Preferably, the expandable element is reversibly expandable with an expandable member of the delivery device.

In another aspect of the invention the expandable element is adapted for engaging an inflatable balloon located on a balloon catheter. Preferably, the expandable element is adapted for engaging an inflatable balloon located adjacent the distal end of a balloon catheter.

In another aspect of the invention the expandable element comprises a sheet material.

In another aspect of the invention the expandable element comprises a perforated is material.

In a further aspect of the invention the expandable element comprises a plastics material.

Alternatively, the expandable element comprises a metal material. Preferably, the expandable element comprises a memory metal. Advantageously, the expandable element comprises nitinol metal.

In another embodiment of the invention the guide element comprises a semi-rigid material. Preferably, the guide element comprises a rigid material.

In one aspect of the invention the guide element comprises a plastics material.

In another aspect of the invention the guide element comprises a metal material.

In a further aspect of the invention the material of the guide element comprises a material similar to that of the expandable element but configured to be non-expandable in the guide element.

Preferably, the anchoring device is configurable for delivery to a site in the lumen or vessel by a catheter.

The invention also provides a combination comprising an anchoring device according to the invention and a boring tool co-operable with the anchoring device for extending through the guide bore of the guide element of the anchoring device.

Preferably, the boring tool comprises a boring element and a carrier element.

Advantageously, the carrier element comprises an elongated carrier wire.

Preferably, the boring element is mounted on a distal end of the carrier wire, and extends therefrom.

Advantageously, the boring element extends coaxially with the carrier element.

In one aspect of the invention one of the boring element and the carrier element is provided with an external screw thread, the external screw thread being adapted to be co-operable with the primary internal screw thread of the anchoring device for urging the boring element relative to the guide element.

Preferably, the boring element comprises a distal boring tip portion.

Advantageously, the external screw thread is provided on the boring element intermediate the boring tip portion thereof and the carrier element.

In one aspect of the invention the combination further comprises a delivery device for delivering the anchoring device to the site in the lumen or vessel.

In another aspect of the invention the delivery device comprises an expandable member mounted thereon, the expandable element of the anchoring device being releasably engageable with the expandable member of the delivery device.

In a further aspect of the invention the delivery device comprises a balloon catheter, and the expandable element of the anchoring device is releasably engageable with the balloon of the balloon catheter.

Preferably, the balloon of the balloon catheter is located adjacent the distal end of the balloon catheter.

Further the invention provides a combination comprising an anchoring device according to the invention and a balloon catheter, the expandable element of the anchoring device being releasably engageable with a balloon of the balloon catheter.

Preferably, the balloon catheter comprises an elongated catheter and the balloon mounted on the catheter.

Advantageously, the balloon of the balloon catheter is located on the catheter adjacent a distal end thereof.

Ideally, the expandable element of the anchoring device is mounted on the balloon of the balloon catheter adjacent the distal end of the balloon.

The invention also provides an adapter for securing to a distal end of a catheter of a balloon catheter, the adapter comprising a guide element defining a guide bore extending therethrough, the guide bore being adapted to accommodate one of a boring tool and a carrier element of the boring tool for guiding the boring tool, a coupling means adapted for coupling the adapter to the catheter, and an engagement means in one of the guide element and the coupling means for engaging one of the boring tool and the carrier element of the boring tool so that the boring tool is urgeable outwardly of the guide element against the adapter.

In one aspect of the invention the engagement means comprises an internal primary screw thread for co-operating with a corresponding external screw thread on one of the boring tool and the carrier element of the boring tool. Preferably, the engagement means is located in the guide bore of the guide element.

In another aspect of the invention the coupling means is adapted for coupling the adapter to the catheter of the balloon catheter adjacent the balloon.

Preferably, the coupling means is adapted for coupling the adapter to the catheter adjacent a distal end of the balloon. Advantageously, the coupling means is adapted for coupling to the distal end of the catheter. Ideally, the coupling means is adapted for coupling the adapter to the catheter adjacent a proximal end of the balloon. Preferably, the coupling means is adapted for releasably coupling the adapter to the balloon catheter.

In another aspect of the invention a communicating bore extends through the coupling means, the communicating bore communicating with the guide bore for accommodating one of the boring tool and the carrier element therethrough to the guide bore, and being adapted to communicate with an elongated bore extending longitudinally through the catheter of the balloon catheter for accommodating one of the boring tool and the carrier element to the guide bore of the guide element from the bore extending through the catheter.

Advantageously, the coupling means comprises a secondary screw thread for releasably securing the adapter to the balloon catheter. Preferably, the secondary screw thread comprises an internal secondary screw thread located in the communicating bore of the coupling means. Advantageously, the secondary screw thread is adapted for forming a corresponding thread on the catheter adjacent the distal end thereof as the coupling means is being threaded onto the distal end of the catheter. Ideally, the secondary screw thread is of an opposite hand to the hand of the primary screw thread.

In another aspect of the invention the coupling means defines a main central axis, which in use is adapted to extend substantially parallel to a longitudinally extending central axis defined by the balloon catheter, and the guide bore of the guide element defines a secondary central axis. Preferably, the guide element is configured relative to the coupling means with the secondary central axis defined by the guide bore of the guide element extending substantially parallel to the main central axis defined by the coupling means. Advantageously, the guide element is configured relative to the coupling means with the secondary central axis defined by the guide bore of the guide element substantially coinciding with the main central axis defined by the coupling means. Alternatively, the guide element is configured relative to the coupling means with the secondary central axis defined by the guide bore of the guide element offset from the main central axis defined by the coupling means.

In another alternative aspect of the invention the guide element is configured relative to the coupling means with the secondary central axis defined by the guide bore of the guide element extending at an angle greater than zero to the main central axis defined by the coupling means. Preferably, the guide element is configured relative to the coupling means with the secondary central axis defined by the guide bore of the guide element extending at an angle between 1° and 90° to the main central axis defined by the coupling means.

In one aspect of the invention the guide element is configured relative to the coupling means with the secondary central axis defined by the guide bore of the guide element extending at an angle between 20° and 35° to the main central axis defined by the coupling means.

In another aspect of the invention the guide element is configured relative to the coupling means with the secondary central axis defined by the guide bore of the guide element extending at an angle between 35° and 55° to the main central axis defined by the coupling means.

In a further aspect of the invention the guide element is configured relative to the coupling means with the secondary central axis defined by the guide bore of the guide element extending at an angle between 55° and 70° to the main central axis defined by the coupling means.

In a still further aspect of the invention the guide element is configured relative to the coupling means with the secondary central axis defined by the guide bore of the guide element extending at an angle of approximately 90° to the main central axis defined by the coupling means.

Preferably, the guide element extends from the coupling means.

In another aspect of the invention the adapter comprises one of a rigid and a semi-rigid material.

In another aspect of the invention the adapter comprises a plastics material.

In an alternative aspect of the invention the adapter comprises a metal material.

The invention also provides a combination comprising an adapter according to the invention and a boring tool co-operable with the adapter for extending through the guide bore of the guide element of the adapter.

In another aspect of the invention the combination further comprises a balloon catheter for delivering the adapter to the site in the lumen or vessel.

Preferably, the adapter is coupled to the catheter of the balloon catheter adjacent a distal end thereof by the coupling means.

In one embodiment of the invention the balloon of the balloon catheter is located adjacent the distal end of the balloon catheter.

The invention also provides a combination comprising an adapter according to the invention, and a balloon catheter comprising an elongated catheter and the balloon mounted on the catheter, the adapter being coupled to the catheter adjacent the distal end thereof by the coupling means.

Additionally the invention provides an anchoring device for anchoring a boring tool at a site in a lumen or vessel, the anchoring device comprising an expandable element adapted for expanding in the lumen or vessel to anchor the anchoring device therein, the expandable element comprising a self-expanding element adapted for delivery to the site through a longitudinally extending delivery bore of a delivery catheter, and being adapted to expand outwardly on being urged out of the delivery bore of the delivery catheter adjacent the site for anchoring the anchoring device in the lumen or vessel adjacent the site, a guide element defining a guide bore extending therethrough to accommodate one of a boring tool and a carrier element of the boring tool for guiding the boring tool, and an engagement means associated with one of the guide element and the expandable element for engaging one of the boring tool and the carrier element of the boring tool, so that the boring tool is urgeable outwardly of the guide element against the anchoring device.

In one aspect of the invention a carrier tube having a bore therethrough extends from the expandable element for accommodating one of the boring tool and the carrier element of the boring tool therethrough to the guide bore of the guide element.

Preferably, the expandable element is located between the carrier tube and the guide element.

Advantageously, the expandable element accommodates the one of the boring tool and the carrier element of the boring tool from the carrier tube to the guide bore of the guide element.

The invention also provide a method for anchoring a boring tool in a lumen or vessel adjacent a remote site, the method comprising locating an anchoring device according to the invention on a delivery device with the expandable element mounted on an expandable member of the delivery device, urging the delivery device with the anchoring device located thereon to the remote site in the lumen or vessel, expanding the expandable member of the delivery device to expand the expandable element of the anchoring device in the lumen or vessel adjacent the remote site for anchoring the anchoring device in the lumen, locating one of the boring tool and the carrier element of the boring tool in the guide bore of the guide element with one of the boring tool and the carrier element engaging the engaging means, and urging the boring tool outwardly of the guide bore of the guide element against the anchoring device.

In one embodiment of the invention the anchoring device is located in the lumen adjacent the remote site with the guide bore of the guide element thereof substantially aligned with an area in which an opening is to be made by the boring tool prior to expanding the expandable element.

In another aspect of the invention the boring tool is urged into engagement with the area in which the opening is to be made for forming the opening therein.

In a further aspect of the invention the anchoring device is urged to a remote site adjacent an occlusion in the lumen or vessel, and the boring tool is urged into engagement with the occlusion for forming an opening through the occlusion.

Additionally the invention provides a method for anchoring a boring tool in a lumen or vessel adjacent a remote site, the method comprising securing an adapter according to the invention on a balloon catheter, urging the balloon catheter with the adapter secured thereto to the remote site in the lumen or vessel, inflating the balloon of the balloon catheter for anchoring the adapter in the lumen or vessel adjacent the remote site, locating one of the boring tool and the carrier element of the boring tool in the guide bore of the guide element with one of the boring tool and the carrier element engaging the engaging means, and urging the boring tool outwardly of the guide bore of the guide element against the adapter.

In another embodiment of the invention the adapter is located in the lumen adjacent the remote site with the guide bore of the guide element thereof substantially aligned with an area in which an opening is to be made by the boring tool prior to inflating the balloon.

In another embodiment of the invention the adapter is urged to a remote site adjacent an occlusion in the lumen or vessel, and the boring tool is urged into engagement with the occlusion for forming an opening through the occlusion.

Further the invention provides a method for anchoring a boring tool in a lumen or vessel adjacent a remote site, the method comprising urging an anchoring device according to the invention through a delivery catheter to the remote site in the lumen or vessel, urging the expandable element of the anchoring device through a distal end of the delivery catheter to expand the expandable element of the anchoring device in the lumen or vessel adjacent the remote site, locating one of the boring tool and the carrier element of the boring tool in the guide bore of the guide element with one of the boring tool and the carrier element engaged in the engaging means, and urging the boring tool outwardly of the guide bore of the guide element against the anchoring device.

In one embodiment of the invention the expandable element is disposed in the distal end of the catheter adjacent the remote site with the guide element extending relative to an area in which an opening is to be made by the boring tool prior to urging the expandable element through the distal end of the delivery catheter, so that on urging the expandable element through the distal end of the delivery catheter into the lumen, the guide bore is aligned with the area in which the opening is to be made.

The invention further provides a balloon catheter comprising an elongated catheter extending from a proximal end to a distal end, and an inflatable balloon located on the catheter, a guide element extending from the catheter adjacent the balloon, the guide element comprising a guide bore extending therethrough for guiding a boring tool therethrough, the guide bore communicating with one of a central lumen of the catheter and a bore extending through an elongated tubular member extending along the catheter for accommodating the boring tool and a carrier element of the boring tool therethrough to the guide bore, and an engagement means for engaging one of the boring tool and the carrier element so that the boring tool is urgeable outwardly of the guide element against the guide element.

In one aspect of the invention the guide element extends from the catheter adjacent a proximal end of the balloon.

In another aspect of the invention the guide element extends from the catheter adjacent a distal end of the balloon.

In a further aspect of the invention the guide element extends at an angle greater than zero from the catheter.

In another aspect of the invention the guide element extends from the catheter at an angle in the range of 1° to 90°.

In a further aspect of the invention the balloon is located adjacent the distal end of the catheter.

The advantages of the invention are many. A particular advantage of the anchoring devices according to the invention is that they can be provided at relatively low cost, and can be readily attached to a conventional balloon catheter or other delivery device, of the type which is readily available in an operating theatre for delivering the anchoring devices to a remote site in a lumen or vessel, and once anchored adjacent the remote site a boring tool can be urged into engagement with and through the occlusion against the anchored anchoring device. This significantly reduces the cost of providing equipment for carrying out procedures for unblocking an occlusion, or for forming an opening in a wall of a lumen or vessel. Similar advantages are achieved by the adapters according to the invention. The anchoring devices and the adapters according to the invention provide a further advantage when the guide element is angled at an angle greater than zero degrees to either the expandable element or the coupling means in that the boring tool can be guided to form an opening through a wall of a lumen or vessel or through an occlusion at an angle to, for example, a central axis of the lumen or vessel.

The advantages of the method according to the invention and to the combinations according to the invention are substantially similar to those just described.

The invention will be more clearly understood from the following description of some preferred embodiments thereof, which are given by way of example only, with reference to the accompanying drawings, in which.

Referring to the drawings and initially to FIGS. 1 to 5 thereof, there is illustrated an anchoring device according to the invention, indicated generally by the reference numeral 1, for providing an anchorage for a boring tool 3 in a lumen 4 at a site 5 adjacent an occlusion 6 in the lumen 4 which is to be opened by the boring tool 3. In this embodiment of the invention the anchoring device 1 is adapted for mounting on a distal end 7 of a delivery device, namely, a balloon catheter 8, as will be described in more detail below, for delivering the anchoring device 1 to the site 5, so that with the anchoring device 1 anchored in the lumen 4, the boring tool 3 can be urged against the anchoring device 1 into and through the occlusion 6 for forming an opening therethrough.

Figure 1:
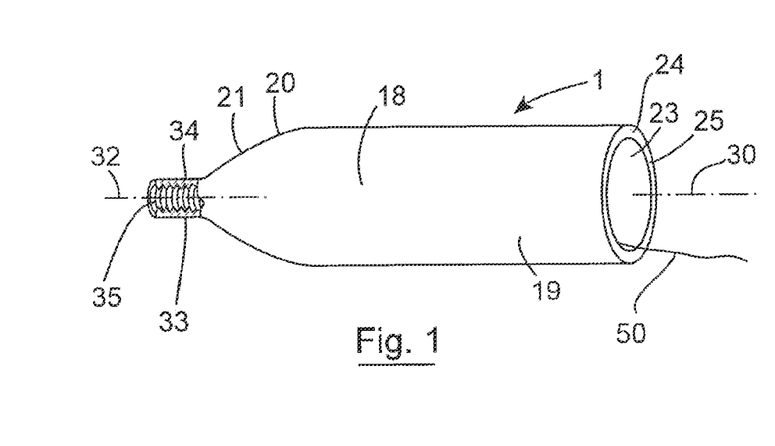
FIG. 1 is a partly cross-sectional perspective view of an anchoring device according to the invention.
Figure 2:
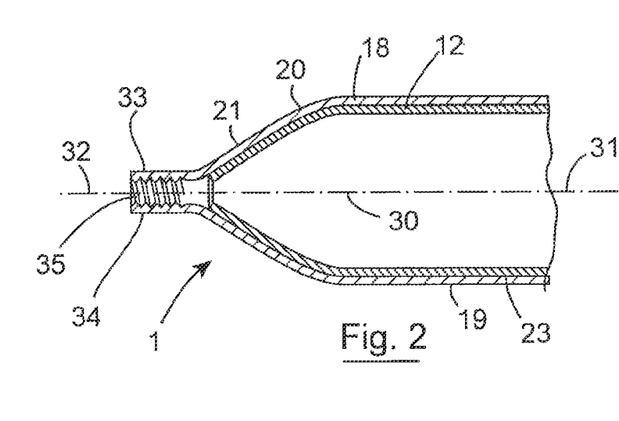
FIG. 2 is a transverse cross-sectional side elevational view of a portion of the anchoring device of FIG. 1 illustrated mounted on a distal end of a balloon catheter.

The balloon catheter 8 comprises an elongated catheter 10 extending between a proximal end 11 and the distal end 7. An inflatable balloon 12 is concentrically located on the catheter 10 adjacent the distal end 7 thereof with the catheter 10 extending through the balloon 12. The balloon 12 is of a resilient expandable plastics material, which is reversibly expandable. The catheter 10 may be of any suitable material. A communicating lumen (not shown) extends through the catheter 10 from the proximal end 11 to the balloon 12 and communicates with the balloon 12 for accommodating an inflating medium, for example, air or a saline solution for inflating and deflating the balloon 12. A main central lumen 15 extends through the catheter 10 from the proximal end 11 to the distal end 7 for accommodating the boring tool 3 therethrough to the anchoring device 1, as will be described below.

The anchoring device 1 comprises an expandable element 18 which is adapted for mounting on the balloon 12 adjacent a distal portion thereof. The expandable element 18 is of tubular construction comprising a side wall 19, terminating at its distal end 20 in a dome shaped end cap 21 which defines with the side wall 19 a hollow interior region 23. The expandable element 18 terminates at its proximal end 24 in an open mouth 25 for accommodating the balloon 12 into the hollow interior region 23. The side wall 19 and the end cap 21 of the expandable element 18 are integrally formed from the same material, which in this embodiment of the invention is a resilient plastics material, which in this case is a latex material and is reversibly expandable and expands and contracts with expansion and contraction of the balloon 12. The expandable element 18 defines a longitudinally extending main central axis 30 which when mounted on the balloon 12 with the balloon 12 inflated substantially coincides with a longitudinally extending central axis 31 defined by the catheter 10 of the balloon catheter 8.

A guide element 33 of a rigid non-expandable plastics material extends outwardly in a general axial direction from the end cap 21 of the expandable element 18. A guide bore 34 extending through the guide element 33 guides the boring tool 3 centrally into and through the occlusion 6. The guide bore 34 defines a secondary central axis 32 which substantially coincides with the main central axis 30 of the expandable element 18. An engagement means, which in this embodiment of the invention comprises an internal primary screw thread 35 in the guide bore 34 for engaging a corresponding external screw thread 36 on the boring tool 3, so that by rotating the boring tool 3 in the guide bore 34 with the external screw thread 36 engaging the primary screw thread 35, and with the anchoring device 1 anchored in the lumen 4, the boring tool 3 is urged outwardly through the guide bore 34 against the anchoring device 1 and into engagement with the occlusion 6 for forming the opening therethrough.

The boring tool 3 comprises a boring element 39 having a distal portion 40 which terminates in a point 41 for piercing the occlusion 6. The external screw thread 36 is provided on a proximal portion 43 of the boring element 39 for co-operating with the primary internal screw thread 35 in the guide bore 34. The boring element 39 is carried on and extends coaxially from a carrier element, which in this embodiment of the invention comprises a carrier wire 45. The carrier wire 45 is of similar material and construction to that of a guide wire of the type for guiding the balloon catheter 8 to the site 5 adjacent the occlusion 6, and extends from the proximal portion 43 of the boring tool 3 through the central lumen 15 of the catheter 10 of the balloon catheter 8 to the proximal end 11 thereof. The carrier wire 45 extends from the proximal end 11 of the catheter 10 for facilitating rotating of the carrier wire 45, for in turn rotating the boring element 39 in the guide bore 34 of the guide element 33 with the external screw thread 36 of the boring element 39 co-operating with the internal primary screw thread 35 in the guide bore 34 for urging the boring element 39 outwardly through the guide bore 34 against the anchoring device 1 and into engagement with the occlusion 6.

Figure 3:
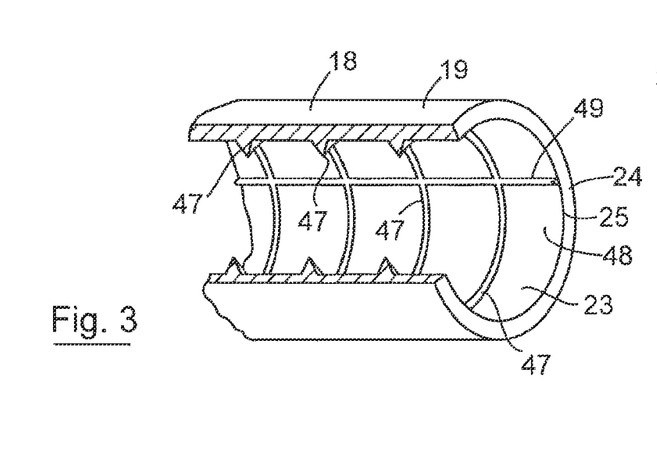
FIG. 3 is a cutaway perspective view of a detail of the anchoring device of FIG. 1.

A securing means for releasably securing the expandable element 18 onto the balloon 12 comprises a plurality of spaced apart circumferentially extending annular ridges 47 located on an internal surface 48 of the expandable element 18, which extend inwardly therefrom into the hollow interior region 23 to engage the balloon 12 and to retain the expandable element 18 on the balloon 12. As discussed above, the expandable element 18 is reversibly expandable, as is the balloon 12, and expands and contracts with the balloon 12, so that the annular ridges 47 of the expandable element 18 remain in engagement with the balloon 12 as the balloon 12 and the expandable element 18 are expanding and contracting in unison. Additionally, the annular ridges 47 remain in engagement with the balloon 12 when the expandable element 18 and the balloon 12 are in a fully contracted state.

A stop means comprising a longitudinally extending ridge 49 extends from the internal surface 48 of the expandable element 18 into the hollow interior region 23 for engaging the balloon 12 of the balloon catheter for preventing rotation of the expandable element 18 on the balloon 12 when the boring tool 3 is being rotated in the guide bore 34 of the guide element 33.

A retrieving means comprising a retrieving wire 50 is connected to the expandable element 18 of the anchoring device 1 adjacent the proximal end 24 thereof for retrieving the anchoring device 1 from the lumen 4 should it become detached from the balloon catheter 8. The retrieving wire 50 is of length similar to or greater than the length of the balloon catheter 8, and extends from the expandable element 18 in the lumen 4 externally along the balloon catheter 8 as the balloon catheter 8 is being urged through the lumen 4. A proximal end 51 of the retrieving wire 50 remains outside the lumen 4 with the proximal end 11 of the balloon catheter 8 to facilitate retrieval of the anchoring device 1 in the event that the anchoring device 1 should become detached from the balloon catheter 8 in the lumen 4.

Figure 4:
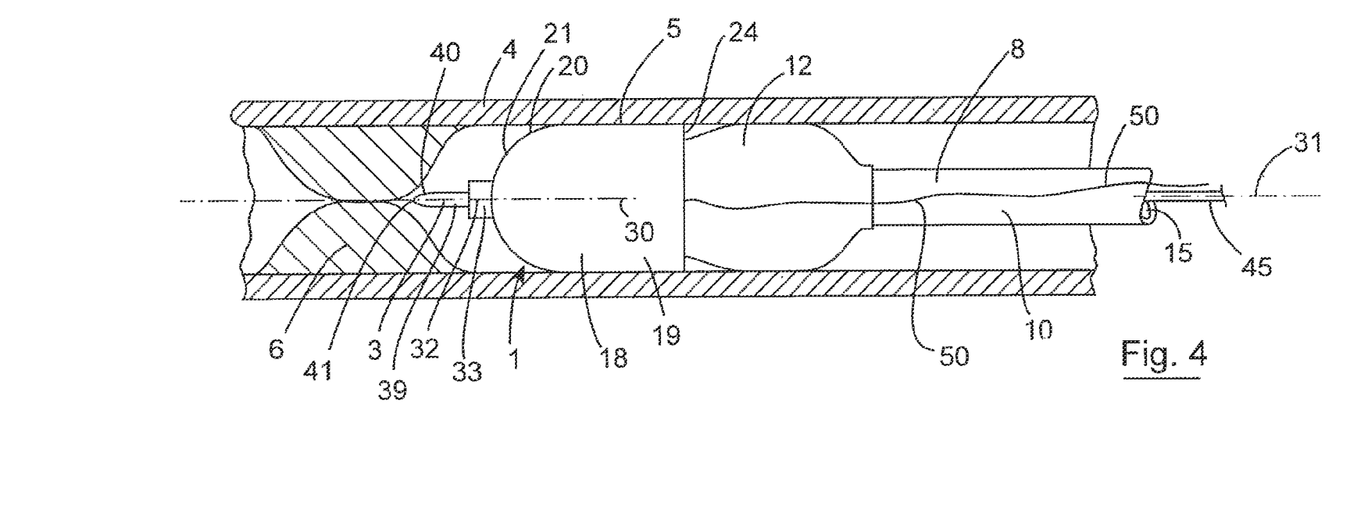
FIG. 4 is a cross-sectional side elevational view of a lumen illustrating the anchoring device mounted on a balloon catheter in use.
Figure 5:
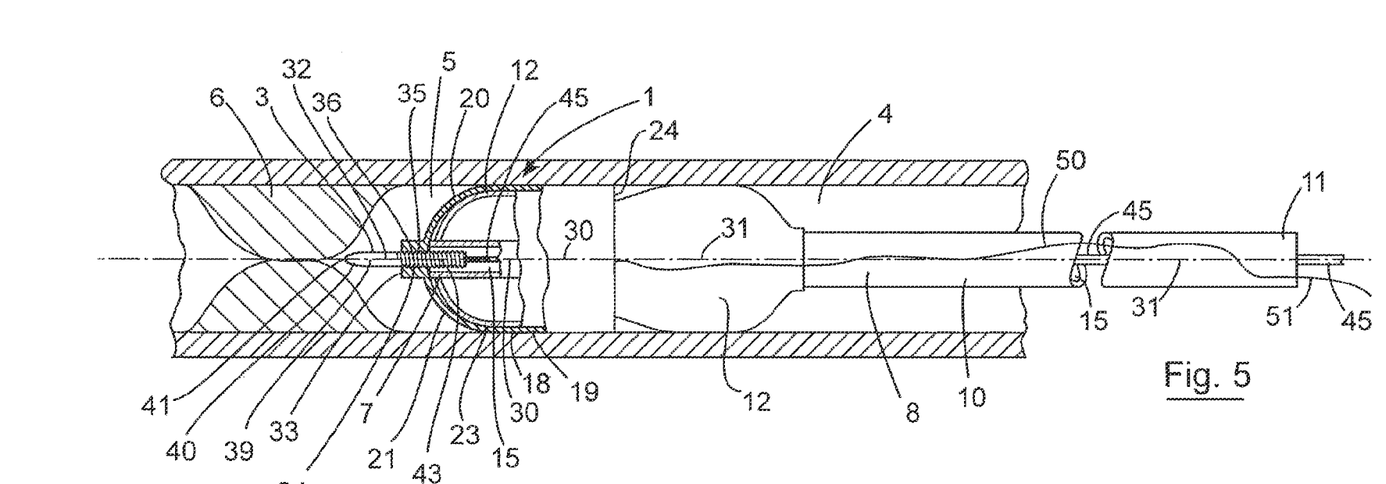
FIG. 5 is a view similar to FIG. 4 but with parts of the anchoring device and the balloon catheter illustrated in cross-section also illustrating the anchoring device and the balloon catheter in use.

In use, the anchoring device 1 is mounted on the balloon 12 adjacent the distal end of the balloon catheter 8 by urging the balloon 12 into the hollow interior region 23 of the expandable element 18 through the open mouth 25 thereof with the balloon 12 deflated. The balloon catheter 8 with the anchoring device 1 mounted thereon is then passed through the lumen 4 in the body of a human or animal to the site 5 therein adjacent the occlusion 6. Typically, the anchoring device 1 is adapted for anchoring the boring tool 3 in the cardiovascular system of the human or animal body for opening an occlusion in an artery of the heart. In which case, the catheter typically is entered into the arterial system of the human or animal body through the femoral artery in the femur of a subject and is guided towards the site 5 adjacent the occlusion 6 in the lumen 4.

Prior to urging the balloon catheter 8 through the arterial system of the human or animal body, a guide wire (not shown) is first inserted through the arterial system to the site 5 in order that the balloon catheter 8 can be guided over the guide wire to the site 5 adjacent the occlusion 6 with the guide wire extending through the central lumen 15 of the catheter 10. With the balloon 12 and the anchoring device 1 located in the site 5 adjacent the occlusion 6, the guide wire (not shown) is withdrawn through the central lumen of the catheter 10. The balloon 12 of the balloon catheter 8 is inflated for expanding the expandable element 18 to engage the lumen 4 at the site 5 for in turn anchoring the anchoring device 1 in the lumen 4.

The boring tool 3 on the carrier wire 45 is then urged through the central lumen 15 of the catheter 10 of the balloon catheter 8 to engage the guide bore 34 of the guide element 33. With the boring element 39 of the boring tool 3 extending outwardly of the guide element 33 towards the occlusion 5, the carrier wire 45 is urged further into the central lumen 15 of the catheter 10 until the external screw thread 36 of the boring element 39 engages the internal primary screw thread 35 in the guide bore 34. With the external screw thread 36 of the boring element 39 engaging the internal primary screw thread 35 in the guide bore 34, the carrier wire 45 is rotated in order to threadingly engage the external screw thread 36 with the internal primary screw thread 35 in the guide bore 34. The carrier wire 45 is then further rotated so that with the external screw thread 36 co-operating with the internal primary screw thread 35, the boring element 39 is urged into engagement with and through the occlusion 6 for forming an opening therethrough.

On the occlusion 6 being opened, the boring element 39 is withdrawn therefrom by rotating the carrier wire 45 in the reverse direction until the external screw thread 36 of the boring element 39 disengages the internal primary screw thread 35 in the guide bore 34 so that the boring tool 3 can be disengaged from the guide element 33 and removed through the central lumen 15 of the catheter 10 of the balloon catheter 8.

Further procedures can then be carried out at the site 5 and to the occlusion 6 which will be well known to those skilled in the art.

Figure 6:
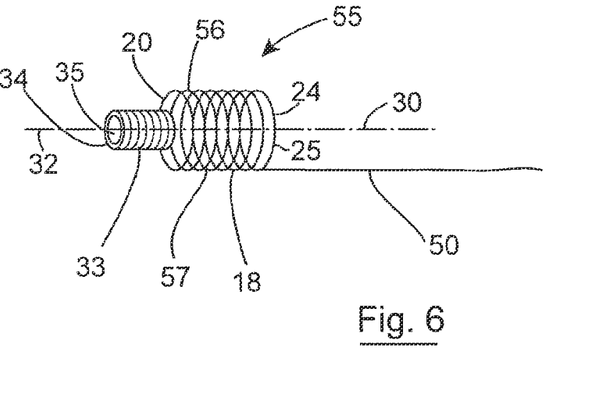
FIG. 6 is a perspective view of an anchoring device according to another embodiment of the invention.

Referring now to FIG. 6, there is illustrated an anchoring device according to another embodiment of the invention, indicated generally by the reference numeral 55, for mounting on the distal end of a balloon catheter for forming an anchorage for a boring tool at a site in a lumen adjacent an occlusion. The balloon catheter and the boring tool in this case are similar to the balloon catheter 8 and the boring tool 3 described with reference to FIGS. 1 to 5. The anchoring device 55 is substantially similar to the anchoring device 1, and similar components are identified by the same reference numerals. The main difference between the anchoring device 55 and the anchoring device 1 is in the expandable element 18. In this embodiment of the invention the expandable element 18 is formed by a resilient flexible expandable element 56 which is formed by a tightly wound coil 57 of a super elastic wire, namely, nitinol. The expandable element 56 is engageable with the balloon of the balloon catheter as the balloon is inflated. The coil 57 of the expandable element 56 is reversibly expandable, so that on deflating of the balloon of the balloon catheter, the coil 57 contracts with the balloon.

Otherwise, the anchoring device 55 and its use is similar to the anchoring device 1.

Figure 7:
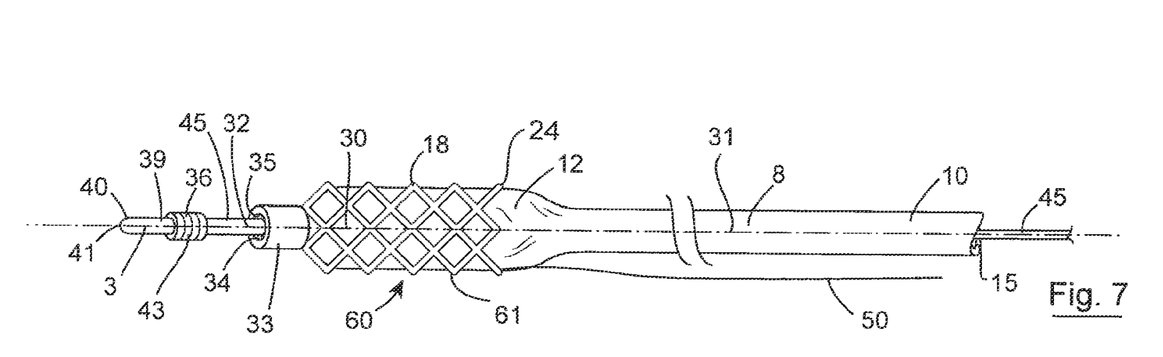
FIG. 7 is a perspective view of an anchoring device according to another embodiment of the invention illustrated mounted on a balloon catheter.
Figure 8:
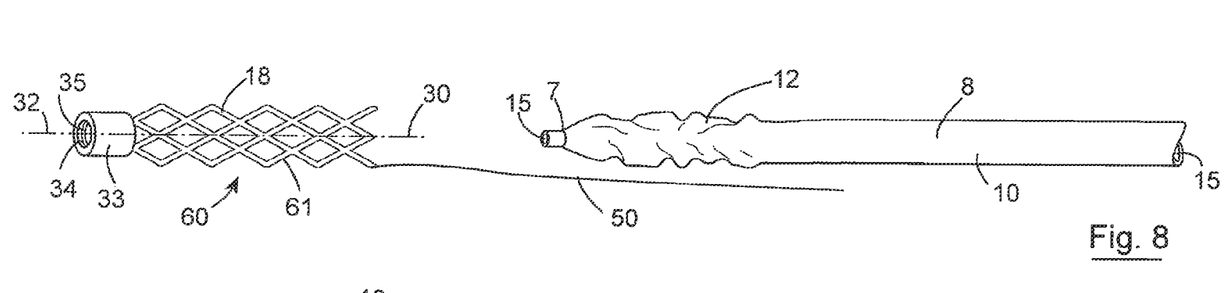
FIG. 8 is a perspective view of the anchoring device and a portion of the balloon catheter of FIG. 7 illustrated prior to the anchoring device being mounted on the balloon catheter.

Referring now to FIGS. 7 and 8, there is illustrated an anchoring device also according to the invention, indicated generally by the reference numeral 60, for mounting on a balloon 12 of a balloon catheter 8 for anchoring a boring tool 3 in a site in a lumen adjacent an occlusion. The balloon catheter 8 and the boring tool 3 are similar to the balloon catheter 8 and the boring tool 3, respectively, described with reference to FIGS. 1 to 5, and similar components are identified by the same reference numerals.

The anchoring device 60 is substantially similar to the anchoring device 1 and similar components are identified by the same reference numerals. The main difference between the anchoring device 60 and the anchoring device 1 is in the expandable element 18. In this embodiment of the invention the expandable element 18 comprises a tubular member 61 of a perforated expandable material. In this embodiment of the invention the tubular member 61 is formed from any of the following expandable materials, namely, materials from which stents are formed, a polymer material or a braided material of wires. The tubular member 61 is reversibly expandable, so that the tubular member 61 expands and contracts with expansion and contraction of the balloon 12. The guide element 33 extends coaxially from the tubular member 61.

Otherwise, the anchoring device 60 and its use is similar to the anchoring device 1.

Figure 9:
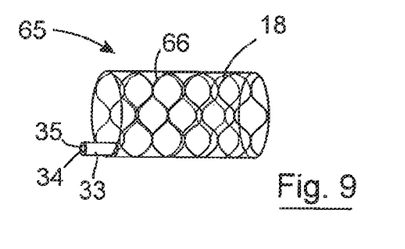
FIG. 9 is a perspective view of an anchoring device according to another embodiment of the invention.
Figure 10:
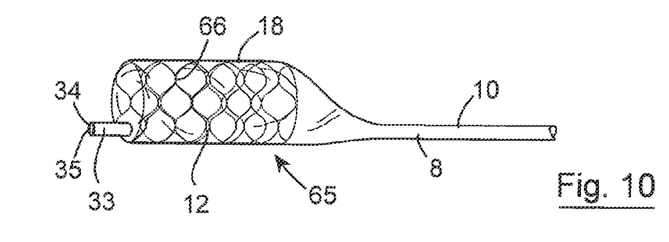
FIG. 10 is a perspective view of a balloon catheter with the anchoring device of FIG. 9 mounted thereon.
Figure 11:
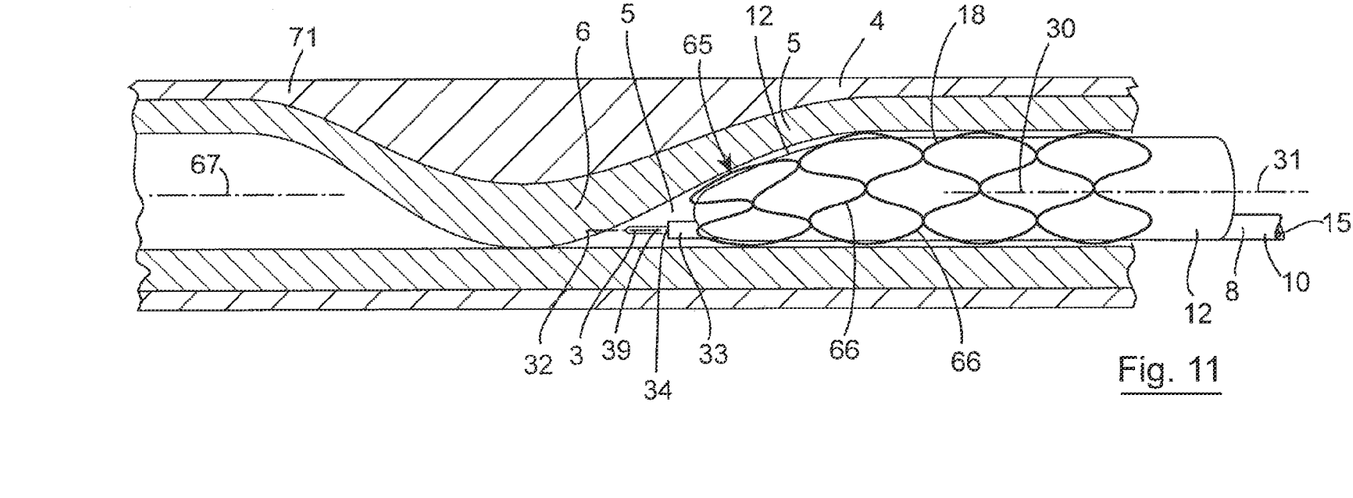
FIG. 11 is a cross-sectional side elevational view of a lumen illustrating the anchoring device of FIG. 9 and the balloon catheter of FIG. 10 in use.

Referring now to FIGS. 9 to 11, there is illustrated an anchoring device according to another embodiment of the invention, indicated generally by the reference numeral 65, for mounting on a balloon 12 of a balloon catheter 8 and for anchoring a boring tool 3 in a lumen 4 so that a boring tool 3 can be urged into an occlusion 6 at a site 5 in the lumen 4 with the boring tool 3 engaging the occlusion 6 offset from a central axis 67 of the lumen 4. The boring tool 3 is similar to the boring tool 3 described with reference to FIGS. 1 to 5, and similar components are identified by the same reference numerals. The anchoring device 65 is substantially similar to the anchoring device 1, and similar components are identified by the same reference numerals.

The main difference between the anchoring device 65 and the anchoring device 1 is in the expandable element 18. Firstly, in this embodiment of the invention the expandable element 18 of the anchoring device 65 comprises a tubular member 66 of wire netting material. The wire netting material is of super-elastic wire, namely, nitinol, and is reversibly expandable with the balloon 12 of the balloon catheter 8. Secondly, the guide element 33 is located within and secured to the tubular member 66, and instead of the guide element 33 extending coaxially from the expandable element 18, the guide element extends parallel to the main central axis 30 defined by the tubular member 66 but are offset from the main central axis 30 of the tubular member 66, with the secondary central axis 32 defined by the guide bore 34 of the guide element 33 extending parallel to and spaced apart from the main central axis 30. Accordingly, in this embodiment of the invention the boring element 39 of the boring tool 3 is guided by the guide bore 34 to engage the occlusion 6 relatively closely to a portion of a side wall of the lumen 4.

In this embodiment of the invention the balloon 12 of the balloon catheter 8 is also offset centrally relative to the catheter 10 of the balloon catheter 8. The amount of offset of the balloon 12 relative to the catheter 10 is similar to the offset of the guide element 33 from the main central axis 30 of the expandable element 18 when the balloon 12 is inflated.

Otherwise, the anchoring device 65 according to this embodiment of the invention is substantially similar to the anchoring device described with reference to FIGS. 1 to 5.

In use, the balloon 12 of the balloon catheter 8 with the expandable element 18 of the anchoring device 65 mounted thereon, and with the guide bore 34 of the guide element 33 aligned with the central lumen 15 of the catheter 10, is located in the site 5 adjacent the occlusion 6 with the balloon 12 deflated. The balloon catheter 8 is maneuvered so that the guide bore 34 of the guide element 33 and in turn the boring tool 3 is aligned with the portion of the occlusion 6 to be pierced by the boring tool 3 for opening the occlusion 6. The balloon 12 of the balloon catheter 8 is then inflated for in turn expanding the expandable element 18 of the anchoring device 65 to engage the lumen 4, and in turn to anchor the anchoring device 65 in the lumen 4. With the anchoring device 65 anchored in the lumen 4, and with the external screw thread 36 of the boring tool 3 engaged in the internal primary screw thread 35 in the guide bore 34, the boring element 39 of the boring tool 3 is advanced into and through the occlusion 6 as already described with reference to the anchoring device 1 of FIGS. 1 to 5.

The advantage of offsetting the guide element 33 from the main central axis 30 of the expandable element 18 is that it facilitates opening an occlusion in a lumen where the occlusion 6 is not centred in the lumen 4. In FIG. 11 the occlusion 6 is illustrated offset from the central axis 67 of the lumen 4 in a coronary artery 71. By rotating the balloon catheter 8 when the balloon catheter 8 with the anchoring device 65 mounted thereon is located in the site 5 adjacent the occlusion 6, the guide element 33 and in turn the boring tool 3 can be aligned in the occlusion 6 in the coronary artery 71 to centrally engage the occlusion 6.

It is well known for an occlusion to be formed in a coronary artery where the occlusion is eccentrically located relative to the central axis 67 or the coronary artery. As a result of the formation of such an eccentrically located occlusion, the true lumen of the artery is off centre within the occlusion. If the boring tool 3 were urged into the occlusion concentrically with the central axis 67 of the artery, the boring tool would penetrate an inner lamina of the artery and would progress between the inner lamina and an outer lamina of the artery. If the boring tool remained between the inner and outer laminae of the artery, when an inflatable balloon of a balloon catheter was urged into the opening in the occlusion to deliver a stent, the balloon when inflated would tear apart the artery, which would lead to a condition known as dissection of the artery. By offsetting the guide element 33 relative to the expandable element 18, the guide element 33 and in turn the boring tool 3 can be located centrally relative to the occlusion 6, thereby avoiding any danger of the boring tool 3 penetrating between the inner and outer laminae of the artery.

Figure 12:
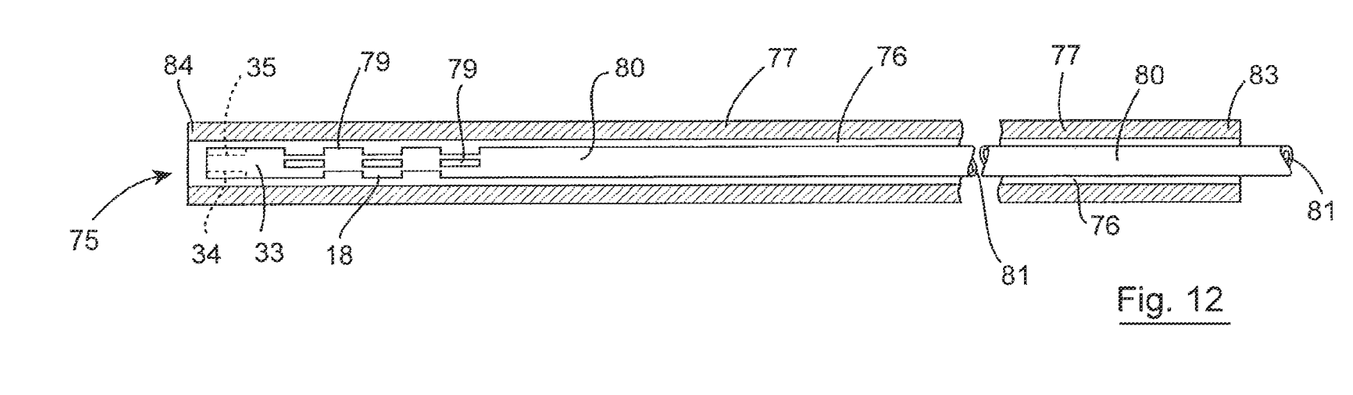
FIG. 12 is a cross-sectional side elevational view of an anchoring device according to another embodiment of the invention located within a catheter.
Figure 13:
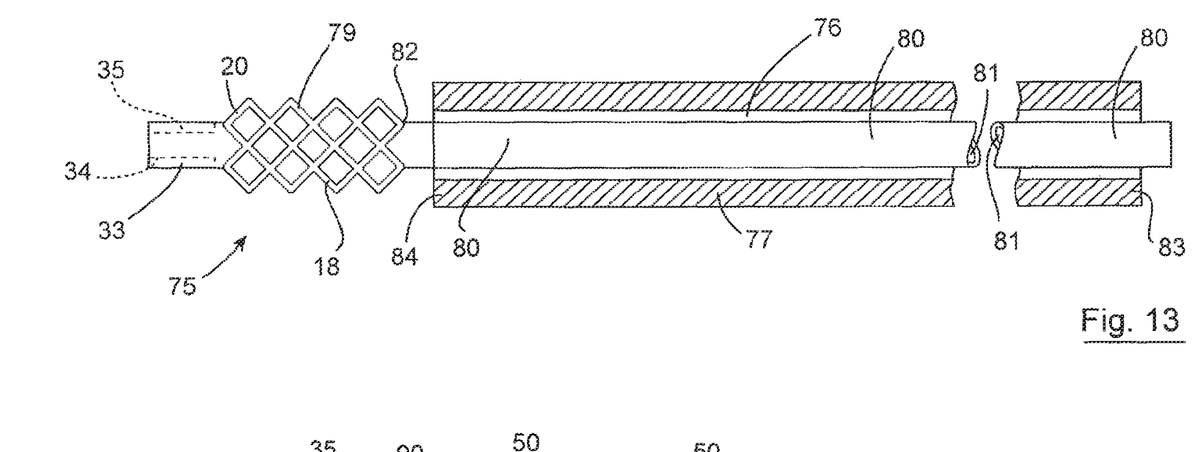
FIG. 13 is a cross-sectional side elevational view of the anchoring device of FIG. 12 in a different state.

Referring now to FIGS. 12 and 13, there is illustrated an anchoring device according to another embodiment of the invention and indicated generally by the reference numeral 75. In this embodiment of the invention the anchoring device 75 is somewhat similar to the anchoring device 1 and similar components are identified by the same reference numerals. However, the main difference between the anchoring device 75 and the anchoring device 1 is that the anchoring device 75 is not adapted for mounting on the distal end of a balloon catheter, but rather, is adapted for delivery to the site in the lumen adjacent the occlusion through a central lumen 76 of a delivery catheter 77. In this embodiment of the invention the expandable element 18 comprises a tubular member 79 of a perforated resilient material which is self-expanding. In this embodiment of the invention the tubular member 79 comprises a memory metal, namely, nitinol. The guide element 33, which is similar to the guide element 33 of the anchoring device 1, extends from the distal end 20 of the tubular member 79 coaxially with the tubular member 79.

An elongated carrier tube 80 extends from a proximal end 82 of the tubular member 79 coaxially with the tubular member 79. The catheter 80 defines an elongated bore 81 to accommodate the boring tool and the carrier wire therethrough for accommodating the boring tool to the guide element 33. The boring tool and the carrier wire are similar to the boring tool 3 and the carrier wire 45, respectively, of the anchoring device 1 of FIGS. 1 to 5. The catheter 80 extends the length of the delivery catheter 77 and extends through a proximal end 83 of the catheter 77 for facilitating manipulating the tubular member 79 into and out of the central lumen 76 of the catheter 77. The memory metal of the tubular member 79 is inherently biased outwardly into an expanded state illustrated in FIG. 13 for engaging the lumen at the site adjacent the occlusion, and for in turn anchoring the anchoring device 75 in the lumen adjacent the occlusion, and is contractible into a contracted state illustrated in FIG. 12 for accommodating the anchoring device 75 through the central lumen 76 of the delivery catheter 77.

The tubular member 79 is retained in the contracted state while in the central lumen 76 of the delivery catheter 77. On being urged outwardly of the central lumen 76 through a distal end 84 of the delivery catheter 77, the tubular member 79 self-expands from the contracted state to the expanded state to engage the lumen, and to anchor the anchoring device 75 in the lumen. On being urged into the central lumen 76 of the delivery catheter 77, the tubular member 79 is urged into the contracted state so that the anchoring device 75 can be withdrawn through the central lumen 76 of the delivery catheter 77.

In use, the delivery catheter 77 is urged through the lumen until the distal end 84 of the delivery catheter 77 is located at the site adjacent the occlusion. This is typically achieved by passing the delivery catheter 77 over a guide wire (not shown), the distal end of which is already located at the site adjacent the occlusion. On the distal end 84 of the delivery catheter 77 being located adjacent the occlusion, the guide wire (not shown) is withdrawn through the central lumen 76 of the delivery catheter 77. The anchoring device 75 is urged through the central lumen 76 of the delivery catheter 77 by urging the carrier tube 80 into the central lumen 76 of the catheter 77 until the tubular member 79 is adjacent the distal end 84 of the delivery catheter 77. Further urging of the carrier tube 80 through the central lumen 76 of the delivery catheter 77 urges the tubular member 79 through the distal end 84 of the delivery catheter 77. As the tubular member 79 exits the central lumen 76 of the delivery catheter 77, the tubular member 79 commences to self-expand into the lumen, to engage the lumen and thus anchor the anchoring device 75 in the lumen in the site adjacent the occlusion.

The boring tool with the carrier wire is then urged through the bore 81 of the carrier tube 80 until the external screw thread on the boring tool engage the internal primary screw thread 35 in the guide bore 34 of the guide element 33. Thereafter rotation of the carrier wire causes the external screw thread of the boring tool to co-operate with the internal primary screw thread 35 of the guide bore 34 for urging the boring tool into engagement with the occlusion for opening thereof.

On completion of the procedure adjacent the occlusion, the tubular member 79 is urged into the central lumen 76 of the delivery catheter 77 by withdrawing the carrier tube 80 through the central lumen 76 of the delivery catheter 77. Urging the tubular member 79 into the central lumen 76 of the catheter 77 urges the tubular member 79 from the expanded state into the contracted state. The anchoring device 75 is then withdrawn through the central lumen 76 of the delivery catheter 77.

Figure 14:
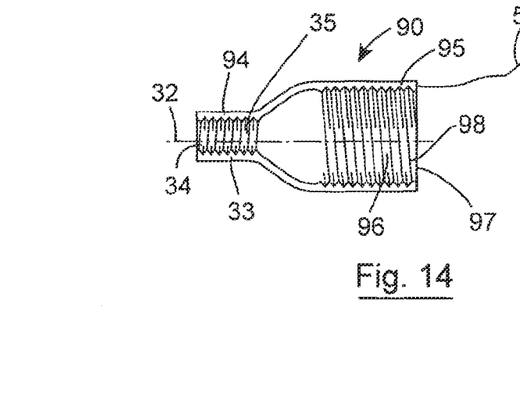
FIG. 14 is an enlarged cross-sectional side elevational view of an adapter according to the invention.
Figure 15:
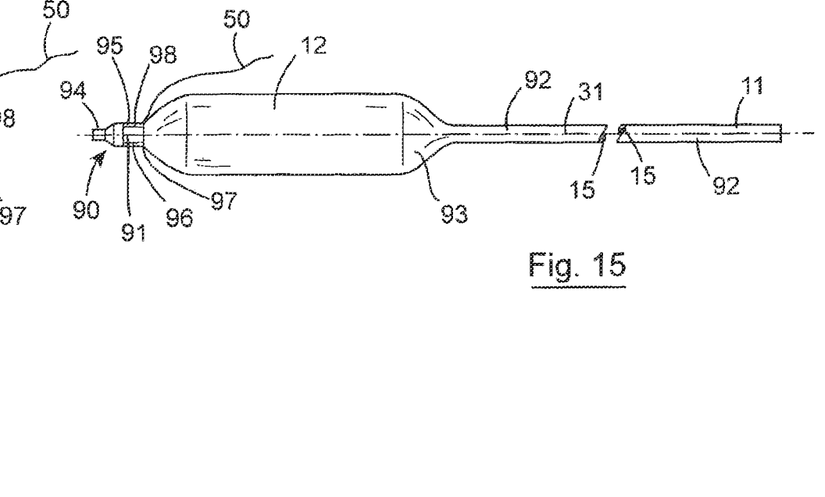
FIG. 15 is a side elevational view of the adaptor of FIG. 14 illustrated mounted on a balloon catheter.

Referring now to FIGS. 14 and 15, there is illustrated an adapter also according to the invention, indicated generally by the reference numeral 90, for securing to a distal end 91 of a catheter 92 of a balloon catheter 93 for anchoring a boring tool at a site adjacent an occlusion in a lumen, for example, an artery in the heart of a subject.

The boring tool in this embodiment of the invention is similar to the boring tool 3 of the anchoring device 1 described with reference to FIGS. 1 to 5. The balloon catheter 93 is substantially similar to the balloon catheter 8 disclosed with reference to the anchoring device 1 of FIGS. 1 to 5, and similar components are identified by the same reference numerals.

The adapter 90 comprises a guide element 94 which is similar to the guide element 33 of the anchoring device 1 of FIGS. 1 to 5, and similar components are identified by the same reference numerals. A coupling means, namely, a tubular coupling element 95 extends rearwardly from the guide element 94 for coupling the adapter 90 to the distal end 91 of the balloon catheter 93. The coupling element 95 and the guide element 94 are integrally formed from the same rigid material, which in this embodiment of the invention is stainless steel, although other suitable rigid materials could be used, for example, metal alloys, such as nitinol. The guide element 94 and the coupling element 95 could also be made from a relatively rigid polymer material or other suitable plastics materials. A communicating bore 96 extends into the coupling element 95 from a proximal end 97 thereof for engaging the distal end 91 of the catheter 92 of the balloon catheter 93, and for communicating the guide bore 34 of the guide element 94 with the central lumen 15 of the balloon catheter 93, for in turn accommodating the boring tool and the carrier wire of the boring tool from the central lumen 15 of the catheter 92 of the balloon catheter 93 to the guide bore 34 of the guide element 94.

A securing means for releasably securing the coupling element 95 on the distal end 91 of the catheter 92 comprises an internal secondary screw thread 98 located within the communicating bore 96 of the coupling element 95 for threading the coupling element 95 onto the distal end 91 of the catheter 92. The internal secondary screw thread 98 of the coupling element 95 are such as to be capable of cutting a corresponding external screw thread onto the distal end 91 of the catheter 92 as the coupling element 95 is being threaded onto the distal end 91 of the catheter 92. Additionally, the internal secondary screw thread 98 in the communicating bore 96 of the coupling element 95 is of opposite hand to the hand of the internal primary screw thread 35 in the guide bore 35 of the guide element 94, so that when the external screw thread of the boring tool is engaged with the internal primary screw thread 35 of the guide element 94, and the boring tool is being rotated for urging into engagement with an occlusion, the rotating action of the boring tool on the adapter 90 acts to tighten the coupling element 95 onto the distal end 91 of the catheter 92 of the balloon catheter 93, thereby avoiding any danger of detachment of the adapter 90 from the distal end 91 of the balloon catheter 93.

A retrieving means, namely, a retrieving wire 50 extends from the proximal end 97 of the coupling element 95 for retrieving the adapter 90 in the event of it becoming detached from the balloon catheter 93.

In use, with the adapter 90 secured by the coupling element 95 to the distal end 91 of the balloon catheter 93, and with the balloon 12 deflated, the balloon catheter 93 is urged through the lumen until the distal end 91 of the catheter 92 is located at the site in the lumen adjacent the occlusion, as has already been described with reference to the anchoring device of FIGS. 1 to 5. The balloon 12 of the balloon catheter 93 is inflated for anchoring the balloon catheter 93 in the lumen, and in turn anchoring the adapter 90 in the lumen adjacent the occlusion. With the adapter 90 so anchored, the boring tool is urged by the carrier wire through the central lumen 15 of the balloon catheter 93 until the external screw thread of the boring tool engages the internal primary screw thread 35 in the guide bore 34 of the guide element 94. With the external thread of the boring tool co-operating with the internal primary screw thread 35 of the guide element 94, the carrier wire of the boring tool is rotated for urging the boring tool into engagement with the occlusion for opening thereof.

Otherwise, the use of the adapter 90 is similar to that of the anchoring device 1 described with reference to FIGS. 1 to 5.

Figures 16, 17, 18:
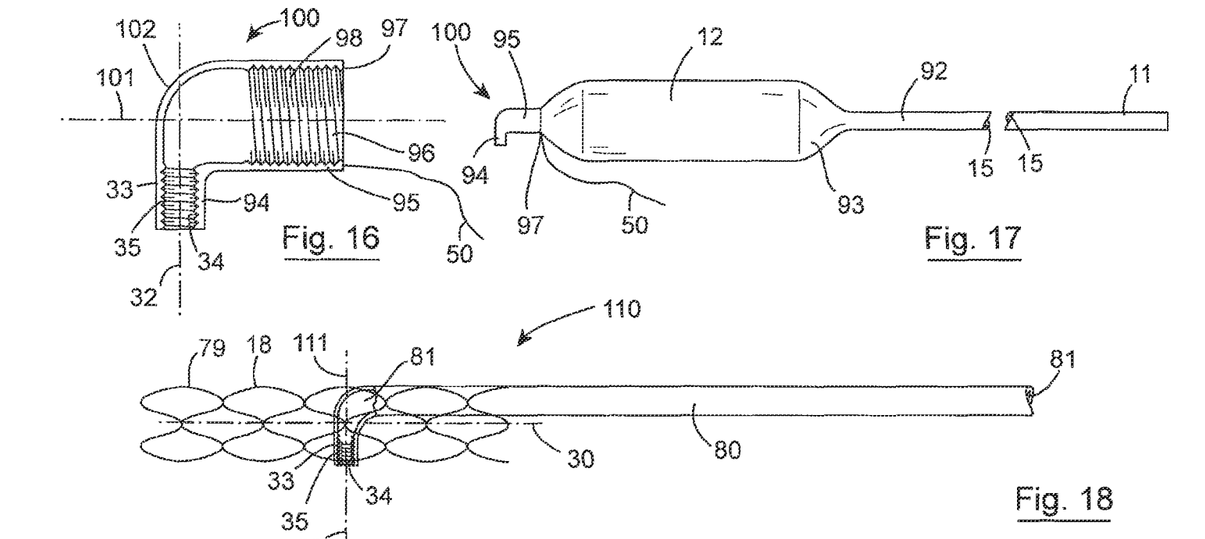
FIG. 16 is an enlarged view similar to that of FIG. 14 of an adapter according to another embodiment of the invention.
FIG. 17 is a view similar to FIG. 15 of the adapter of FIG. 16 illustrated mounted on a balloon catheter.
FIG. 18 is a side elevational view of an anchoring device according to another embodiment of the invention.

Referring now to FIGS. 16 and 17, there is illustrated an adapter according to another embodiment of the invention, indicated generally by the reference numeral 100 for securing to the distal end 91 of a catheter 92 of the balloon catheter 93 for anchoring a boring tool similar to the boring tool 3 at a site adjacent an occlusion in a lumen. The balloon catheter 93 is substantially similar to the balloon catheter 93 described with reference to the adapter 90 of FIGS. 14 and 15, and similar components are identified by the same reference numerals. The adapter 100 is substantially similar to the adapter 90 described with reference to FIGS. 14 and 15, and similar components are identified by the same reference numerals. The main difference between the adapter 100 and the adapter 90 is that the guide element 94 extends at an angle greater than zero from the coupling element 95, and in this embodiment of the invention extends at 90° relative to the coupling element 95, in other words, transversely of the coupling element 95. Accordingly, the secondary central axis 32 defined by the guide bore 34 of the guide element 94 extends at 90° relative to a main central axis 101 defined by the communicating bore 96 of the coupling element 95.

In use, with the adapter 100 secured to the distal end 91 of the balloon catheter 93, and with the balloon catheter 93 located in the lumen with the distal end 91 of the catheter 92 adjacent the occlusion, the balloon 12 of the balloon catheter 93 is inflated. The boring tool 3 is urged by the carrier wire through the central lumen 15 of the balloon catheter 93 and into the coupling element 95. On engaging a wall 102 of the adapter 100, the boring tool is urged through 90° into the guide bore 34 of the guide element 94. Further urging of the boring tool into the guide bore 34 of the guide element 94 results in the external screw thread of the boring tool engaging the internal primary screw thread 35 in the guide bore 34. Thereafter, rotation of the boring tool by rotating the carrier wire urges the boring tool outwardly of the guide element 94 into engagement with the occlusion for opening thereof.

Otherwise, the adapter 100 and its use is similar to the adapter 90 described with reference to FIGS. 14 and 15.

The advantage of the adapter 100 is that it permits the boring tool to be located at a site in a vessel, lumen or artery with the boring tool aligned with a specific site in a wall of the vessel, lumen or artery for boring through the wall thereof. The adapter 100 is particularly suitable for facilitating boring through a wall or a partition wall of or within the heart or other organ. The adapter 100 is also suitable for use in denerving a site in a kidney adjacent a wall of a lumen or vessel in the kidney in a procedure for treating high blood pressure.

Referring now to FIG. 18, there is illustrated an anchoring device according to another embodiment of the invention, indicated generally by the reference numeral 110. The anchoring device 110 is substantially similar to the anchoring device 75, and similar components are identified by the same reference numerals. The main difference between the anchoring device 110 and the anchoring device 75 is that the guide element 33 is coupled to the carrier tube 80, is located within the expandable element 18, and extends transversely relative to the main central axis 30 of the expandable element 18. In other words, the secondary central axis 32 defined by the guide bore 34 of the guide element 33 extends at an angle of 90° to the main central axis of the expandable element 18. Accordingly, the guide bore 34 of the guide element 33 directs the boring tool transversely of the expandable element 18.

Otherwise, the anchoring device 110 and its use is similar to that of the anchoring device 75 described with reference to FIGS. 12 and 13, with the exception that the boring tool is urged by the carrier wire through the bore 81 of the carrier tube 80 directly into the guide element 33. On the boring tool engaging a wall 111 of the guide element 33, the boring tool is directed through an angle of approximately 90° into the guide bore 34 of the guide element 33. The boring tool is urged by the carrier wire further into the guide bore 34 of the guide element 33 for engaging the external screw thread of the boring tool with the internal primary screw thread 35 in the guide bore 34 of the guide element 33. Thereafter the boring tool is rotated by the carrier wire for in turn urging the boring tool outwardly into engagement with a wall of the vessel or lumen in which an opening is to be formed, as already described with reference to the adapter 100 which is described with reference to FIGS. 16 and 17.

The advantages of the anchoring device 110 are similar to those achieved by the adapter 100, which has been described with reference to FIGS. 16 and 17.

Figure 19:
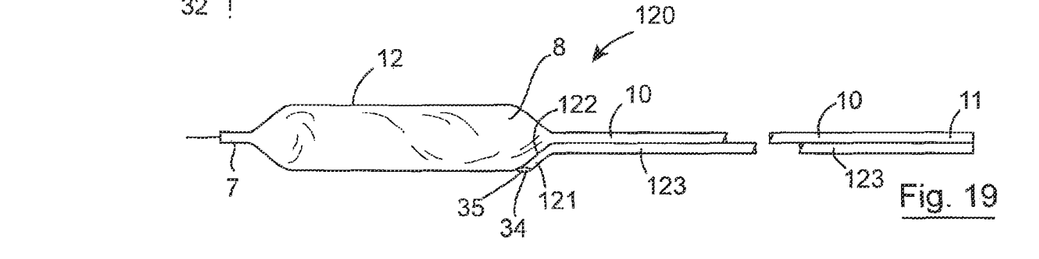
FIG. 19 is a side elevational view of a balloon catheter according to the invention.

Referring now to FIG. 19, there is illustrated a balloon catheter also according to the invention, indicated generally by the reference numeral 120. The balloon catheter 120 is substantially similar to the balloon catheter 8 described with reference to the anchoring device 1 of FIGS. 1 to 5, and similar components are identified by the same reference numerals. However, in this embodiment of the invention a guide element 121 is secured to and extends from the catheter 10 of the balloon catheter 120 adjacent the proximal end 122 of the balloon 12 thereof. The guide element 121 is similar to the guide element 33 of the anchoring device 1 described with reference to FIGS. 1 to 5, and similar components are identified by the same reference numerals. The guide element 121 extends from the catheter 10 at an angle of approximately 60°, and is adapted for guiding a boring tool similar to the boring tool 3 into a side wall of a vessel, lumen, artery or the like.

An elongated carrier tube 123 extends along the catheter 10 of the balloon catheter 120 for accommodating the boring tool and the carrier wire therethrough to the guide element 121. Alternatively, the guide element 121 could be secured to the catheter 10 of the balloon catheter 120 with the guide bore 34 of the guide element 121 communicating directly with the central lumen 15 of the balloon catheter 120. In which case, the central lumen 15 of the balloon catheter 120 would terminate in the guide bore 34 of the guide element 121, and would be adapted to direct the boring tool into the guide bore 34 of the guide element 121. Accordingly, in this embodiment of the invention the secondary central axis 32 defined by the guide bore 34 of the guide element 121 extends at an angle greater than zero, which in this embodiment of the invention is approximately 60° relative to the main central axis 30 of the main central lumen 15 of the balloon catheter 120.

In use, with the balloon catheter 120 located in the lumen and with the guide bore 34 of the guide element 121 aligned with a site in a wall of the lumen through which an opening is to be formed, the balloon 12 of the balloon catheter 120 is inflated for anchoring the balloon catheter, and in turn the guide element 121 in the lumen or vessel. The boring tool is urged through the carrier tube 123 and into the guide bore 34 of the guide element 121. Further urging of the boring tool into the guide bore 34 of the guide element 121 engages the external screw thread of the boring tool with the internal primary screw thread 35 in the bore 34 of the guide element 121. Thereafter, rotating the boring tool by rotating the carrier wire urges the boring tool outwardly through the guide bore 34 of the guide element 121 and into engagement with the wall of the lumen for forming the opening therethrough.

While the anchoring devices, the adapters, the catheters and the balloon catheters have been described as being of specific materials, the anchoring devices, adapters, the catheters and the balloon catheters may be of any suitable materials.

It will be appreciated that the anchoring devices described with reference to FIGS. 1 to 13, instead of being provided with an axially extending guide element, may be provided with a transversely extending guide element, which would extend transversely relative to the main central axis 30 of the expandable elements. Indeed, it is envisaged that the guide element may extend from the expandable element at any angle greater than zero degrees to the main central axis 30 of the expandable element. It is also envisaged that the guide elements of the anchoring devices, the adapters, and the balloon catheter 120 may also extend at any angle relative to the central axis defined by the coupling element or the main central axis defined by the main central lumen 15 of the balloon catheter.

While the securing means for releasably securing the expandable element of the anchoring device of FIGS. 1 to 5 to the balloon of the balloon catheter has been described as comprising a plurality of longitudinally spaced apart annular ridges located on the internal surface of the expandable element, any other suitable securing means may be provided, and in certain cases, it is envisaged that the securing means may comprise an internal secondary screw thread formed on the inner surface of the expandable element, which would engage the outer surface of the balloon of the balloon catheter. Typically, the hand of the internal secondary screw thread on the expandable element would be opposite to the hand of the internal primary screw thread in the guide bore of the guide element so that rotation of the boring tool in the guide bore for urging the boring tool outwardly therefrom would result in tightening of the expandable element onto the balloon of the balloon catheter.

While the balloon catheter 120 has been described as comprising a guide element extending from the catheter adjacent the proximal end of the balloon, it is envisaged that the guide element could instead extend from the catheter adjacent the distal end of the balloon.

While the anchoring device has been described as comprising a stop means for preventing rotation of the expandable element on the balloon of the balloon catheter during rotation of the boring tool in the guide bore, while this is advantageous, it is not essential, and in certain cases, the stop means may be omitted altogether. Alternatively, any other suitable stop means may be provided.

While the anchoring device of FIGS. 1 to 5 has been described as comprising a securing means for releasably securing the expandable element to the balloon of the balloon catheter, and the securing means has been described as comprising annular rings extending internally into the expandable element, any other suitable securing means may be provided. For example, it is envisaged that the annular ridges need not necessarily extend completely around the inner surface of the expandable element. A number of circumferentially spaced apart ridges may be provided, or in certain cases, a single ridge only may be provided. It is also envisaged that other suitable releasable securing means may be provided, for example, the expandable element may be provided with a friction type surface which would have a relatively high coefficient of friction when engaged with the balloon of the balloon catheter. Indeed, in certain cases, it is envisaged that the securing means may be omitted.

The invention claimed is:

1. An anchoring system for anchoring a boring tool at a site in a lumen or vessel, the anchoring system comprising:
   an anchoring device for anchoring the boring tool at the site in the lumen or vessel, and
   a delivery device for delivering the anchoring device to the site in the lumen or vessel, the delivery device comprising:
      an expandable member mounted thereon,
   the anchoring device comprising:
   an expandable element adapted for expanding in the lumen or vessel to anchor the anchoring device therein, the expandable element being releasably mountable on and engageable with the expandable member of the delivery device for delivering the anchoring device to the site in the lumen or vessel, the expandable element defining a main central axis and being expandable with the expandable member of the delivery device for anchoring the anchoring device adjacent the site in the lumen or vessel,
   a securing means located on the expandable element engageable with the expandable member for securing the expandable element to the expandable member and for retaining the expandable element secured to the expandable member during expanding of the expandable element by the expandable member, a guide element defining a guide bore extending therethrough to accommodate one of a boring tool and a carrier element of the boring tool for guiding the boring tool, the guide bore defining a secondary central axis extending at an angle greater than 0° to the main central axis defined by the expandable element, and
   an engagement means located in the guide element and engageable with one of the boring tool and the carrier element of the boring tool so that the boring tool is urgeable outwardly of the guide element against the anchoring device.

2. An anchoring system as claimed in claim 1 in which the expandable element is of a resilient material.

3. An anchoring system as claimed in claim 1 in which the guide element extends from the expandable element and is connected thereto.

4. An anchoring system as claimed in claim 1 in which the guide element is located within the expandable element and is connected thereto.

5. An anchoring system as claimed in claim 1 in which the engagement means comprises an internal primary screw thread located in the guide bore of the guide element.

6. An anchoring system as claimed in claim 5 in which the primary screw thread is adapted for engaging a corresponding external screw thread on one of the boring tool and the carrier element of the boring tool.

7. An anchoring system as claimed in claim 1 in which the engagement means is located in the guide bore of the guide element.

8. An anchoring system as claimed in claim 1 in which the securing means is provided for releasably securing the expandable element to the expandable member of the delivery device.

9. An anchoring system as claimed in claim 1 in which the expandable element is contractible with contraction of the expandable member of the delivery device.

10. An anchoring system as claimed in claim 1 in which the expandable member of the delivery device comprises an inflatable balloon located on an elongated catheter.

11. An anchoring system as claimed in claim 1 in which the expandable element comprises a perforated material.

12. An anchoring system as claimed in claim 1 in which the expandable element comprises a memory metal.

13. An anchoring system for anchoring a boring tool at a site in a lumen or vessel, the anchoring system comprising:
    an anchoring device for anchoring the boring tool at the site in the lumen or vessel, and
    a delivery device for delivering the anchoring device to the site in the lumen or vessel, the delivery device comprising:
       an expandable member mounted thereon,
    the anchoring device comprising:
    an expandable element adapted for expanding in the lumen or vessel to anchor the anchoring device therein, the expandable element being releasably mountable on and engageable with the expandable member of the delivery device for delivering the anchoring device to the site in the lumen or vessel, the expandable element defining a main central axis and being expandable with the expandable member of the delivery device for anchoring the anchoring device adjacent the site in the lumen or vessel,
    a securing means located on the expandable element engageable with the expandable member for securing the expandable element to the expandable member and for retaining the expandable element secured to the expandable member during expanding of the expandable element by the expandable member,
    a guide element defining a guide bore extending therethrough to accommodate one of a boring tool and a carrier element of the boring tool for guiding the boring tool, the guide bore defining a secondary central axis offset from the main central axis defined by the expandable element, and
    an engagement means located in the guide element engageable with one of the boring tool and the carrier element of the boring tool so that the boring tool is urgeable outwardly of the guide element against the anchoring device.

14. An anchoring system as claimed in claim 13 in which the guide element is configured relative to the expandable element with the secondary central axis defined by the guide bore of the guide element extending substantially parallel to the main central axis defined by the expandable element.

15. A boring system comprising:
    a boring tool,
    a carrier element carrying the boring tool,
    an external screw thread formed on one of the boring tool and the carrier element, an anchoring device for anchoring the boring tool at a site in a lumen or vessel, and
    a delivery device for delivering the anchoring device to the site in the lumen or vessel, the delivery device comprising:
       an expandable member mounted thereon,
    the anchoring device comprising:

an expandable element adapted for expanding in the lumen or vessel to anchor the anchoring device therein, the expandable element being releasably mountable on and engageable with the expandable member of the delivery device for delivering the anchoring device to the site in the lumen or vessel, the expandable element defining a main central axis and being expandable with the expandable member of the delivery device for anchoring the anchoring device adjacent the site in the lumen or vessel, a securing means located on the expandable element engageable with the expandable member for securing the expandable element to the expandable member and for retaining the expandable element secured to the expandable member during expanding of the expandable element by the expandable member, a guide element defining a guide bore extending therethrough to accommodate the one of the boring tool and the carrier element of the boring tool for guiding the boring tool, the guide bore defining a secondary central axis extending at an angle greater than 0° to the main central axis defined by the expandable element, and an engagement means comprising an internal screw thread formed in the guide bore of the guide element engageable with the external screw thread of the one of the boring tool and the carrier element so that by rotating the boring tool, the boring tool is urgeable outwardly of the guide bore of the guide element against the anchoring device.

16. A boring system comprising:

a boring tool, a carrier element carrying the boring tool, an external screw thread formed on one of the boring tool and the carrier element, a delivery device for delivering the anchoring device to the site in the lumen or vessel, the delivery device comprising an expandable member mounted thereon, and an anchoring device for anchoring the boring tool at a site in a lumen or vessel, the anchoring device comprising:

an expandable element adapted for expanding in the lumen or vessel to anchor the anchoring device therein, the expandable element defining a main central axis and being releasably mountable on and engageable with the expandable member of the delivery device for delivering the anchoring device to the site in the lumen or vessel, the expandable element being expandable with the expandable member for anchoring the anchoring device adjacent the site in the lumen or vessel, a securing means located on the expandable element engageable with the expandable member for securing the expandable element to the expandable member and for retaining the expandable element secured to the expandable member during expanding of the expandable element by the expandable member, a guide element defining a guide bore extending therethrough to accommodate the one of the boring tool and the carrier element for guiding the boring tool, the guide bore defining a secondary central axis offset from the main central axis defined by the expandable element, and an engagement means comprising an internal screw thread formed in the guide bore of the guide element engageable with the external screw thread of the one of the boring tool and the carrier element so that by rotating the boring tool, the boring tool is urgeable outwardly of the guide bore of the guide element against the anchoring device.

17. A boring system as claimed in claim 16 in which the secondary central axis extends parallel to the main central axis.

* * * * *